(12) United States Patent
Lewis et al.

(10) Patent No.: US 11,007,112 B2
(45) Date of Patent: May 18, 2021

(54) STIMULATION DEVICE

(71) Applicant: Hot Octopuss Ltd, London (GB)

(72) Inventors: Adam Lewis, London (GB); Julia Margo, London (GB)

(73) Assignee: Hot Octopuss Ltd, London (GB)

( * ) Notice: Subject to any disclaimer, the term of this patent is extended or adjusted under 35 U.S.C. 154(b) by 79 days.

(21) Appl. No.: 16/279,303

(22) Filed: Feb. 19, 2019

(65) Prior Publication Data

US 2020/0261305 A1 Aug. 20, 2020

(51) Int. Cl.
| | |
|---|---|
| *A61H 19/00* | (2006.01) |
| *A61F 5/41* | (2006.01) |
| *A61N 1/36* | (2006.01) |
| *A61H 23/02* | (2006.01) |
| *A61H 23/00* | (2006.01) |

(52) U.S. Cl.
CPC .............. *A61H 19/32* (2013.01); *A61F 5/41* (2013.01); *A61F 2005/417* (2013.01); *A61H 23/004* (2013.01); *A61H 23/0218* (2013.01); *A61N 1/36007* (2013.01)

(58) Field of Classification Search
CPC .......... A61F 5/41; A61H 23/004; A61H 19/32
USPC ........................................................... 600/38
See application file for complete search history.

(56) References Cited

U.S. PATENT DOCUMENTS

| | | | | |
|---|---|---|---|---|
| 5,693,002 | A | * | 12/1997 | Tucker ...................... A61F 5/41 600/38 |
| 2002/0022760 | A1 | * | 2/2002 | Orten ........................ A61F 5/41 600/38 |
| 2015/0141748 | A1 | * | 5/2015 | Campbell .............. A61H 19/32 600/38 |

* cited by examiner

*Primary Examiner* — Samuel G Gilbert
(74) *Attorney, Agent, or Firm* — Barnes & Thornburg LLP

(57) ABSTRACT

A device for stimulating the male genitalia. The device includes an elasticated ring configured to encircle a penis. The elasticated ring houses: an electrical power source; a first electrically-powered vibratory part in a top end portion of the ring; a second electrically-powered vibratory part in a bottom end portion of the ring, the top end portion of the ring being opposite the bottom end portion of the ring; and an electrical connection electrically connecting the first and second vibratory parts to the electrical power source. The electrical connection configured to accommodate expansion of the elasticated ring.

13 Claims, 3 Drawing Sheets

STIMULATION DEVICE

The present invention relates to a device which provides stimulation of the male genitalia. More specifically, the invention relates to a stimulation device for putting around a user's penis.

There are a wide variety of devices which are already available which seek to stimulate the male genitalia through a variety of means, either for medical purposes, such as sperm collection or to assist those suffering from erectile dysfunction, or simply for pleasure.

A large range of products has been developed and marketed with a recreational purpose, what are commonly referred to as sex-toys. These devices seek to stimulate the male genitalia in order to give pleasure.

Despite the fact that it is known that vibrations applied to the penis can cause arousal and result in orgasm and ejaculation, there are relatively few products which are actually designed to stimulate the penis through vibrations. The majority of male sex toys are 'sleeves' which fit over the penis and are moved by hand. However, there are various types of penis rings which are designed to fit around the base of the penis, some of which are adapted to deliver vibrations to the penis.

SUMMARY OF THE INVENTION

According to a first aspect of the present invention, there is provided a stimulation device comprising an elasticated ring configured to encircle a penis, wherein the elasticated ring houses: an electrical power source; a first electrically-powered vibratory part in a top end portion of the ring; a second electrically-powered vibratory part in a bottom end portion of the ring, the top end portion of the ring being opposite the bottom end portion of the ring; and electrical connection means electrically connecting the first and second vibratory parts to the electrical power source, and wherein the electrical connection means are configured to accommodate expansion of the elasticated ring.

Embodiments may provide a vibratory penis ring device for stimulating male genitalia. The device may comprise: a single electrical power source; and two vibratory parts configured to generate vibrations and situated at opposing ends of the penis ring. An electrical connection between the electrical power source and the two vibratory parts may accommodate expansion (e.g. stretching, deforming, extension or reshaping) of the ring. In this way, when the device is being manipulated to be fitted on (or removed from) a user's penis, the integrity of an electrical connection between the single power source and the vibratory parts may be maintained. This may facilitate the provision of vibrations to opposing sides of a user's penis, whilst only employing a single electrical power source (e.g. at one position in the device). The device may therefore be lightweight (e.g. by avoiding the use of two separate electrical power sources) whilst also providing for an improved user experience.

The elasticated ring may be made from a malleable material which transmits vibrations and enables the ring to be expanded, stretched or changed in size and shape so as to be fitted on and encircle a penis. Being elasticated, the ring may be adapted to return to an original shape after removal of a deformation force applied to the ring (e.g. as may be done when the ring is expanded, stretched or changed in size and shape to be fitted on a penis).

The elasticated ring may be configured to permit expansion of the ring (e.g. to be fitted on a penis) by more than 10% in at least one direction (and preferably more than 25%, and even more preferably more than 50%) whilst also enabling the elasticated ring to automatically return to an original size and shape after a force causing expansion of the ring has been removed. Expansion of the ring may comprise an increase in size of the ring in a least one direction by at least 10%, and preferably more than 25%. By way of example, the elasticated ring may comprise ABS/Silicone material.

The electrical connection means may be configured to move from a contracted configuration to an expanded configuration as the elasticated ring is expanded, wherein, in the expanded configuration, the longitudinal extent of the electrical connection means is larger than when in the contracted configuration. In this way, an electrical connection from the first and second vibratory parts to the electrical power source may be maintained when the ring is expanded, stretched or changed in size and shape (e.g. when being fitted on a penis).

The electrical connection means may comprise an electrically-conductive flexible wire configured as a helical coil. Such a helical arrangement of the flexible wire may enable a longitudinal extent of the wire to be altered (e.g. moved between an expanded configuration and a contracted configuration) without stretching or breaking the wire.

The electrical connection means may comprise first and second electrically conductive elements that are slidably coupled so as to enable movement of the first and second electrically conductive elements relative to each whilst maintaining electrical connection between the first and second electrically conductive elements. Such a slide arrangement may enable a longitudinal extent of the wire to be altered (e.g. moved between an expanded configuration and a contracted configuration) without stretching or breaking the electrically conductive elements.

The elasticated ring may define a generally circular aperture for insertion of a penis therein, and the top end portion of the ring may be diametrically opposite the bottom end portion of the ring. In this way, during use of the device, the first and second electrically-powered vibratory parts may be provided at opposite sides (e.g. top and bottom) of the user's penis. Vibrations may therefore be delivered to opposing side of the user's penis for improved user experience.

The first electrically-powered vibratory part may comprise a first motor which is configured to be powered by the electrical power source, via the electrical connection means, to generate vibrations, and the second electrically powered vibratory part may comprise a second motor which is configured to be powered by the electrical power source, via the electrical connection means, to generate vibrations.

Further, the first electrically-powered vibratory part may comprise an eccentric weight mounted to a rotatable shaft of the first motor, and the second electrically-powered vibratory part may comprise an eccentric weight mounted to a rotatable shaft of the second motor. Also, the eccentric weights employed by the first and second vibratory parts may be substantially the same size and mass. However, in some embodiments, the eccentric weight of the first electrically-powered vibratory part may be of larger mass than the eccentric weight of the second electrically-powered vibratory part.

At least one of the first and second electrically-powered vibratory parts may be configured to generate vibrations of variable frequency and/or amplitude.

In some embodiments, the first and second electrically-powered vibratory parts may be configured to generate vibrations of a first and second frequency, respectively, and the first frequency may be different from the second frequency. In particular, the first electrically-powered vibratory part may be configured to generate vibrations of a first frequency within a first range of frequencies, and the second electrically-powered vibratory part may be configured to generate vibrations of a second frequency within a second, different range of frequencies. The first frequency may be within the range of 2 kHz to 7 kHZ and the second frequency may be within the range of 2 kHz to 90 kHz.

The electrical power source may comprise a battery. Preferably, the battery may be rechargeable.

Thus, there may be provided a method for stimulating the male genitalia for pleasure, the method comprising using a device according to a proposed embodiment.

According to another aspect of the invention, there is provided a stimulation device comprising an elasticated ring configured to be fitted over a penis and testicles, wherein the elasticated ring houses: an electrical power source; a first electrically-powered vibratory part in a top end portion of the ring; a second electrically-powered vibratory part in a bottom end portion of the ring, the top end portion of the ring being opposite the bottom end portion of the ring; and electrical connection means electrically connecting the first and second vibratory parts to the electrical power source, and wherein the electrical connection means are configured to accommodate expansion of the elasticated ring.

Proposed embodiments may provide a lightweight device, which when attached to the penis (or penis and testicles), delivers vibrations to two different sides of the user's genitalia simultaneously. For example, embodiments may provided a device which, in use, provide vibrations to the top and bottom of (i.e. above and below) the user's penis whilst only employing a single electrical power source at one location within the device. Also, when fitted around the penis and testicles, embodiments may provide vibrations to the perineum and the top of the user's penis. In particular, provision of electrical connection means that are configured to accommodate expansion of the elasticated ring may enable separate vibratory parts to be provided at opposing ends (e.g. top and bottom) of the elasticated ring whilst ensuring that electrical connection of a single power source to both vibratory parts can be maintained, even when the elasticated ring is expanded (e.g. stretched or deformed) to be fitted on (or removed from) a user's penis.

Embodiments may have the following attributes:
Hands-free.
Can be used when the penis is still flaccid.
Adapted to apply vibrations to the base of the penis.
Adapted to apply vibrations to the base of the penis and the perineum.
Provide adjustable amplitude and frequency.
Battery powered, so cheap to maintain.
Compact and lightweight so easily transported.

DETAILED DESCRIPTION

Figure 1:
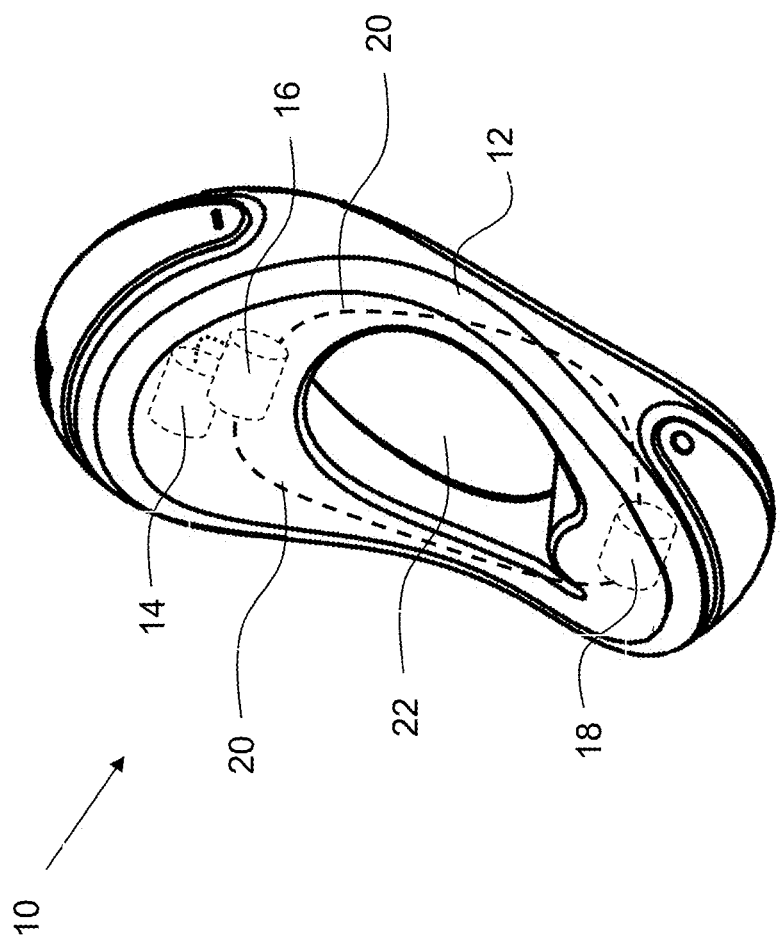
FIG. 1 is a simplified illustration of a stimulation device according to an embodiment.

The invention will be described with reference to the Figures. It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The present invention relates to a simple and easy to use stimulation (or stimulatory) device which can deliver vibrations to the base or shaft of the penis. The vibrations may be delivered to opposing sides (e.g. top and bottom) of the penis (or to the penis and the perineum). The device may comprise an elasticated ring which houses an electrical power source and two electrically-powered vibratory parts at opposing sides of the ring. The ring may also house electrical connection means that electrically connect the electrical power source to the two electrically-powered vibratory parts. The electrical connection means may accommodate expansion of the elasticated ring to ensure that electrical connection is be maintained when the elasticated ring is expanded (e.g. stretched or deformed) to be fitted on (or removed from) a user's penis. This may enable the separate vibratory parts to be provided at opposing ends of the ring even though a single power source is provided for both vibratory parts. Use of a single power source may enable the weight of the device to be minimised although two separate vibratory parts are provided for improved user experience.

The device may be a hands-free device, so that a user does not have to manually hold or manipulate the device during use. For example, some embodiments of the device are intended to provide a hands-free device and be fitted to around the base of a penis (or around the testicles and the base of the penis) during use. The size and weight of the part of the device which is held against the base of the penis is therefore preferably small and lightweight. Ideally, the ring is adapted to be soft and/or malleable and of minimum weight and/or structural integrity to securely hold the power source and vibratory parts in place and transmit vibrations to the penis in use. However, it may be preferable to ensure that the ring is not so small or lightweight that any small movement during use could render it less effective.

The elasticated ring may be preferably formed from a material which has one or more of the following properties, and most preferably all of them: easy to clean; hypoallergenic; not heat conducting; high elasticity; and high malleability. For example, in one embodiment, the elasticated ring may comprise ABS or a silicone material. Suitable materials will be well-known to a skilled person.

A vibratory part may employ one or more motors. Such a motor employed by embodiments may preferably be small and lightweight. It may also be preferable for such a motor to be capable of producing vibrations of variable frequency and/or amplitude (although, in some embodiments, vibrations may be produced only at a single, fixed frequency). Low frequency of vibrations produced by a vibratory part may preferably by up to 7 kHz, whereas a high frequency of vibrations produced by vibratory part may preferably be over 7 kHz (preferably up to 150 kHz, and more preferably up to 90 kHz).

The vibratory parts may be controlled by a control panel (or control unit), allowing the user to adjust the first and second frequencies. In some embodiments, the control panel may also be configured to allow the user to adjust an amplitude of the vibrations and/or a pattern of the vibrations.

In some embodiments, the control panel may be totally detached from the vibrating part (e.g. wirelessly connected to the vibrating part), providing "remote control" of the device.

The device of the invention is preferably battery operated. It would be particularly convenient for the electrical power source battery to be a rechargeable battery, with the device having a charger or a charging station to allow it to be charged between uses.

For a fuller understanding of the proposed concepts, reference is now made to the accompanying drawings, which are intended to illustrate exemplary embodiments described and claimed herein and is not intended to be limiting.

Figure 2:
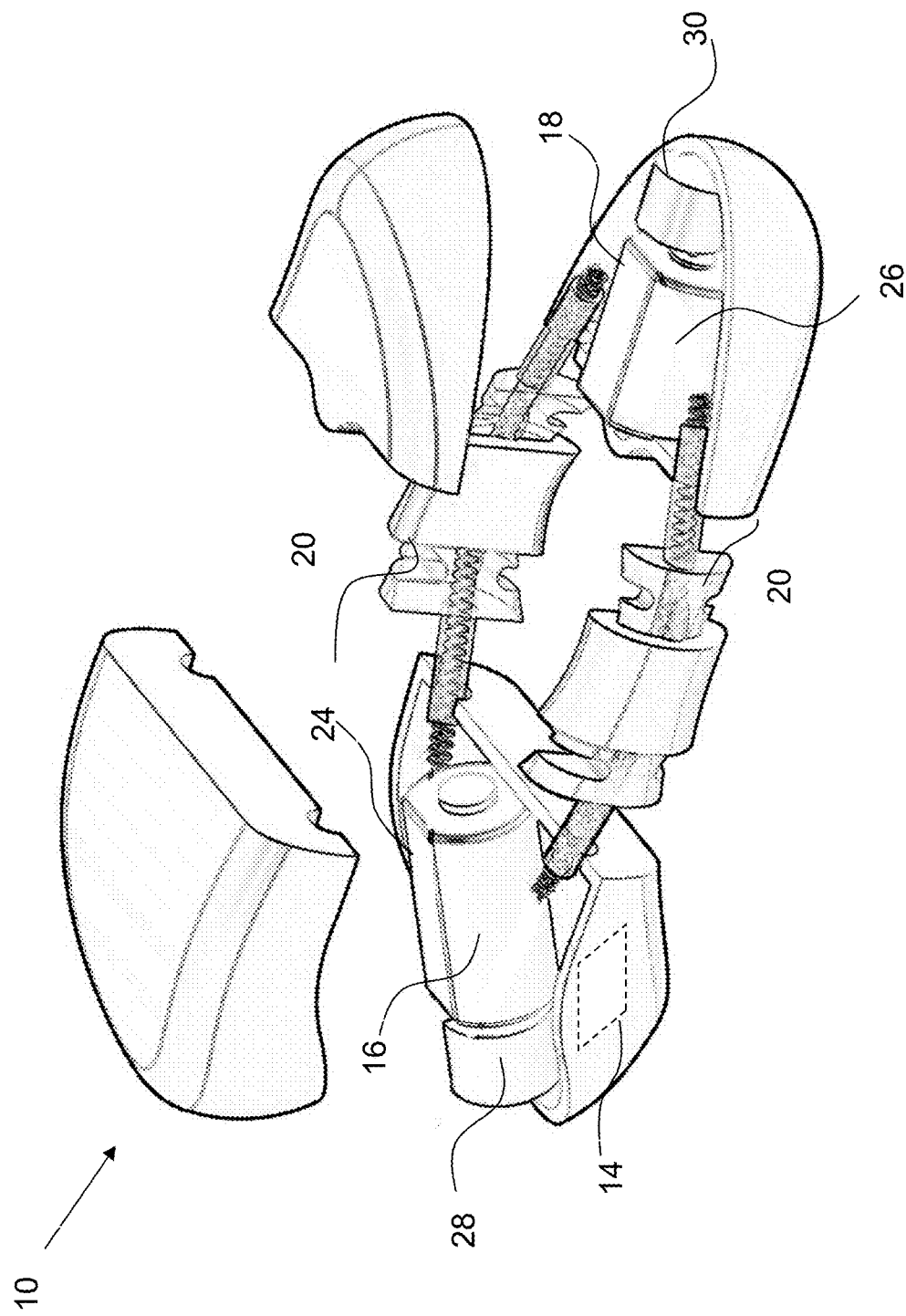
FIG. 2 is an exploded diagram of the device of FIG. 1.

Referring now to FIGS. 1-2, there is depicted a stimulation device 10 according to an embodiment. Specifically, FIG. 1 is an illustration of the stimulation device 10 wherein some of the internal features are depicted using dashed lines. FIG. 2 is an exploded diagram of the device 10 of FIG. 1.

The stimulation device 10 is configured for fitting around a penis and stimulating the base and/or shaft of the penis in use. The device 10 comprises an elasticated ring 12 that is configured to encircle the penis.

Within the elasticated ring 12 there is provided: an electrical power source 14 (such as a battery); a first electrically-powered vibratory part 16 in a top end portion of the ring 12; a second electrically-powered vibratory part 18 in a bottom end portion of the ring 12, the top end portion of the ring being opposite the bottom end portion of the ring; and electrical connection means 20 electrically connecting the first 16 and second 18 vibratory parts to the electrical power source 14.

The elasticated ring 12 defines a generally circular aperture 22 for insertion of a penis therein. The top end portion of the ring 12 is diametrically opposite to the bottom end portion of the ring 12.

The elasticated ring 12 of this embodiment is made from a malleable material which transmits vibrations and enables the ring 12 to be expanded, stretched or changed in size and shape so as to be fitted on and encircle a penis. Being elasticated, the ring may be adapted to return to its original shape (depicted in FIG. 1) after removal of a deformation force applied to the ring (e.g. as may be done when the ring is being expanded, stretched or changed in size and shape to be fitted on a penis).

The elasticated ring 12 is thus configured to permit its expansion (e.g. to be fitted on a penis) by more than 10% in at least one direction (and preferably more than 25%, and even more preferably more than 50%) whilst also enabling the elasticated ring to automatically return to its original size and shape after a force causing its expansion has been removed. Expansion of the ring may entail an increase in size of the ring in a least one direction by at least 10%, and preferably more than 25%.

The first electrically-powered vibratory part 16 is configured to generate vibrations of a first frequency F1 within a first range of frequencies, and the second electrically-powered vibratory part 18 is are configured to generate vibrations of a second frequency F2 within a second, different range of frequencies. In this exemplary embodiment, the first frequency F1 is within the range of 2-7 kHZ (and may be referred to as a 'low frequency'). Further, the second frequency F2 is within the range of 7-90 kHz (and may be referred to as a 'high frequency').

In this example embodiment, the first electrically-powered vibratory part 16 comprises a first motor 24 which is configured to be powered by the electrical power source 14, via the electrical connection means 20, to generate vibrations. Further, the second electrically-powered vibratory part 18 comprises a second motor 26 which is configured to be powered by the electrical power source 14, via the electrical connection means, to generate vibrations.

Also, the first electrically-powered vibratory part 16 comprises an eccentric weight 28 mounted to a rotatable shaft of the first motor 24, and second electrically-powered vibratory part 18 comprises an eccentric weight 30 mounted to a rotatable shaft of the second motor 26.

In this exemplary embodiment, the eccentric weight 28 of the first electrically-powered vibratory part 16 is larger in size and mass than the eccentric weight 30 of the second electrically-powered vibratory part 18. In this way, the larger/heavier weight employed by the first vibratory part 16 assists in making the vibrations generated by the first vibratory part 16 have lower frequency than those generated by the second vibratory part 18 (which employs a smaller/lighter mass).

However, it will be appreciated that, in other embodiments, the eccentric weight 28 of the first electrically-powered vibratory part 16 may be of the same size and mass as the eccentric weight 30 of the second electrically-powered vibratory part 18.

The electrical connection means 20 are configured to accommodate expansion of the elasticated ring 12 (e.g. when the ring 12 is deformed or stretched to be fitted on a penis). In particular, the electrical connection means 20 are configured to move from a contracted configuration (having a first longitudinal extent) to an expanded configuration (having a second, larger longitudinal extent) when the elasticated ring is expanded. In the expanded configuration, the longitudinal extent of the electrical connection means 20 is larger than the longitudinal extent of the electrical connection means 20 when in the contracted configuration.

More specifically, in this embodiment, the electrical connection means 20 comprise a electrically-conductive flexible wire 20 arranged in the form of a helical coil.

The helical coil arrangement of the flexible wire 20 the electrically connects the power source 14 to the first 16 and second 18 vibratory parts is therefore configured to accommodate expansion (e.g. stretching, deforming or reshaping) of the ring 12. In this way, when the device 10 is manipulated to be fitted on (or removed from) a user's penis, the electrical connection between the power source 14 and the first 16 and second 18 vibratory parts is maintained. This facilitates the provision of first 16 and second 18 vibratory parts at opposing ends of the ring 12 with only a single power source 14 (e.g. at one position in the device 10).

Although the embodiment described above has been detailed as employing an electrically-conductive flexible wire arranged in the form of a helical coil, it is envisaged that other embodiments may employ different electrical connection means that are configured to accommodated expansion of the ring whilst maintaining the electrical connection between the power source and the first and second vibratory parts.

By way of example, alternative embodiments may employ first and second electrically conductive elements that are slidably coupled so as to enable movement of the first and second electrically conductive elements relative to each whilst maintaining electrical connection between the first and second electrically conductive elements.

Also, due to being elasticated and accommodating expansion, a device according to an embodiment may be configured for fitting around a penis and the testicles so that it stimulates both the base of the penis and the perineum during use. In such examples, the dual vibratory system may be configured such that the one vibratory part (situated at the bottom of the ring) delivers vibrations to the perineum while the other vibratory part (situated at the top of the rig) delivers vibrations to the base/shaft of the penis (and partner during sexual intercourse).

Figure 3:
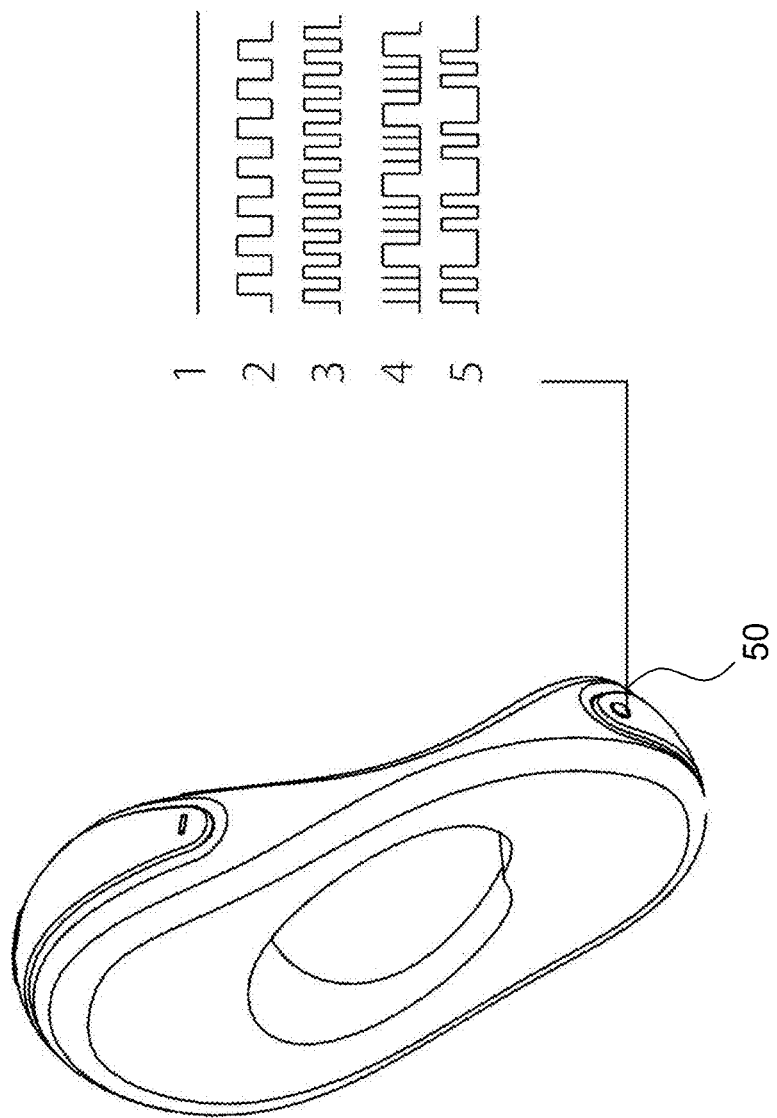
FIG. 3 illustrates how a device according to an embodiment may be controlled to modify a pattern of generated vibrations.

Other modifications or variations to the embodiments described above are envisaged. For example, referring to FIG. 3, the device comprises a user interface 50 for receiving user inputs for controlling the vibratory parts. Here, the user interface is configured to enable a pattern of generated vibrations to be controlled. As depicted by the illustrated power signals (labelled "1" to "5") supplied to the vibratory parts, the user interface 50 may be configured to switch vibrations on or off in various different patterns. This may offer a personalised and varied usage experience to a user.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A stimulation device comprising an elasticated ring configured to encircle a penis,
   wherein the elasticated ring houses:
   an electrical power source;
   a first electrically-powered vibratory part in a top end portion of the ring;
   a second electrically-powered vibratory part in a bottom end portion of the ring, the top end portion of the ring being opposite the bottom end portion of the ring; and
   electrical connection means electrically connecting the first and second vibratory parts to the electrical power source, and
   wherein the electrical connection means are configured to accommodate expansion of the elasticated ring.

2. The stimulation device of claim 1, wherein the electrical connection means are configured to move from a contracted configuration to an expanded configuration as the elasticated ring is expanded, wherein, in the expanded configuration, the longitudinal extent of the electrical connection means is larger than when in the contracted configuration.

3. The stimulation device of claim 1, wherein the electrical connection means comprise an electrically-conductive flexible wire arranged as a helical coil.

4. The stimulation device of claim 1, wherein the electrical connection means comprises first and second electrically conductive elements that are slidably coupled so as to enable movement of the first and second electrically conductive elements relative to each whilst maintaining electrical connection between the first and second electrically conductive elements.

5. The stimulation device of claim 1, wherein the elasticated ring defines a generally circular aperture for insertion of a penis therein, and wherein the top end portion of the ring is diametrically opposite the bottom end portion of the ring.

6. The stimulation device of claim 1, wherein the first electrically-powered vibratory part comprises a first motor which is configured to be powered by the electrical power source, via the electrical connection means, to generate vibrations, and wherein the second electrically powered vibratory part comprises a second motor which is configured to be powered by the electrical power source, via the electrical connection means, to generate vibrations.

7. The stimulation device of claim 6, wherein the first electrically-powered vibratory part comprises an eccentric weight mounted to a rotatable shaft of the first motor, and wherein the second electrically-powered vibratory part comprises an eccentric weight mounted to a rotatable shaft of the second motor.

8. The stimulation device of claim 7, wherein the eccentric weight of the first electrically-powered vibratory part is of larger mass than the eccentric weight of the second electrically-powered vibratory part.

9. The stimulation device of claim 1, wherein at least one of the first and second electrically-powered vibratory parts is configured to generate vibrations of variable frequency and/or amplitude.

10. The stimulation device of claim 1, wherein the first and second electrically-powered vibratory parts are configured to generate vibrations of a first and second frequency, respectively, and wherein the first frequency is different from the second frequency.

11. The stimulation device of claim 1, wherein the first electrically-powered vibratory part is configured to generate vibrations of a first frequency within a first range of frequencies, and wherein the second electrically-powered vibratory part is configured to generate vibrations of a second frequency within a second, different range of frequencies.

12. The stimulation device of claim 1, wherein the electrical power source comprises a battery, and wherein the battery is rechargeable.

13. A stimulation device comprising an elasticated ring configured to be fitted over a penis and testicles,
   wherein the elasticated ring houses:
   an electrical power source;
   a first electrically-powered vibratory part in a top end portion of the ring;
   a second electrically-powered vibratory part in a bottom end portion of the ring, the top end portion of the ring being opposite the bottom end portion of the ring; and
   electrical connection means electrically connecting the first and second vibratory parts to the electrical power source, and
   wherein the electrical connection means are configured to accommodate expansion of the elasticated ring.

* * * * *